US005932436A

United States Patent [19]
Dodson et al.

[11] Patent Number: 5,932,436
[45] Date of Patent: Aug. 3, 1999

[54] DAPHNIA REPRODUCTIVE BIOASSAY FOR TESTING TOXICITY OF AQUEOUS SAMPLES AND PRESENCE OF AN ENDOCRINE DISRUPTER

[75] Inventors: Stanley I. Dodson, Cottage Grove, Wis.; Jonathan B. Shurin, Chicago, Ill.; Kristin M. Girvin, Madison, Wis.

[73] Assignee: Wisconsin Alumni Research Foundation, Madison, Wis.

[21] Appl. No.: 08/762,382

[22] Filed: Dec. 6, 1996

[51] Int. Cl.$^6$ .............................. C12Q 1/00; C12Q 1/02; G01N 33/53
[52] U.S. Cl. ................................. 435/29; 435/4; 435/967
[58] Field of Search ................................... 435/4, 29, 967

[56] References Cited

U.S. PATENT DOCUMENTS

| | | | |
|---|---|---|---|
| 4,965,202 | 10/1990 | Haley et al. | 435/170 |
| 5,169,777 | 12/1992 | Haley et al. | 435/252.1 |
| 5,416,005 | 5/1995 | Blankenmeyer | 435/29 |
| 5,481,815 | 1/1996 | Murphy et al. | 37/344 |
| 5,518,636 | 5/1996 | Petrille, III et al. | 210/749 |
| 5,665,555 | 9/1997 | Sweeney et al. | 435/7.21 |
| 5,672,470 | 9/1997 | Hengstenberg et al. | 435/4 |

OTHER PUBLICATIONS

Hanazato and Dodson, J. Plankton Res. vol. 14 (12), pp. 1743–1755. Abstract enclosed, 1992.

Hanazato and Dodson, J. Plankton Res. vol. 15 (9), pp. 1087–1095. Abstract enclosed, 1993.

Dodson et al. Environ. Toxicol. Chem. vol. 14 (1), pp. 43–50, Abstract enclosed. 1993.

Hanazato and Dodson. Limnol.Oceanog. vol. 40 (4), pp. 700–709. Abstract enclosed, 1995.

American Society for Testing and Materials (ASTM), ASTM Standard Guide for Conducting Renewal Life–Cycle Toxicity Tests With *Daphnia Magna*, Method E, ASTM Publication Code No. 03–547093–16, ASTM, Phildaelphia, PA, pp. 1193–87 (1988).

Colborn et al., Environmental and Health Perspectives 101 (5): 378–384, Developmental Effects of Endocrine–Disrupting Chemicals in Wildlife and Humans, (1993).

Lampert, Int. Revue ges Hyrdobiol 66 (3) 285–298; Inhibitory and Toxic Effects of Bluegreen Algae on Daphnia, (1981).

U.S. EPA. Environmental monitoring and assessment program: Great Lakes monitoring and research strategy. Office of Research and Development, Environmental Research Laboratory–Duluth, Duluth, MN 55804; pp. i to vii; 2–7 to 2–9, 4–1 to 4–38, B–14, and B18–B–20 (1992).

Shurin, Jon, Toxicity and Environmental Sex Determination in Daphnia, submitted to the U.S. Environmental Protection Agency (EPA), Dec. 1995.

ASTM, ASTM Standards on Aquatic Toxicology and Hazard Evaluation, ASTM Publication Code No. 03–547093–16, ASTM, Philadelphia, PA, pp. 151–167 (1993).

U.S. Environmental Protection Agency, Short–Term Methods for Estimating the Chronic Toxicity of Effluents and Receiving Waters to Freshwater Organisms, EPA/600/4–91/002, Lewis et al. (eds.), Cincinnati, OH (Jul. 1994).

Soto et al., in Adavances in Modern Environmental Toxicology 21:295–309, Chemically–Induced Alterations in Sexual and Functional Development: The Wildlife/Human Connection, Colburn & Clement (eds.), Princeton Scientific Publishing Co., Inc., Princeton, NJ (1992).

Bhatnagar–M–C et al, in Journal of Environmental Biology 9(3 Suppl): 283–288 Abstract: Toxicity of a Few Pesticides to a Freshwater Teleost, Clarias Batrachus (LINN) (1988).

Snell et al., Environmental Toxicology and Chemistry 14 (3): 415–420, Comparative Toxicant Sensitivity of Sexual and Asexual Reproduction in the Rotifer *Brachionus Calyciflorus* (1995).

Shurin et al., American Society of Limnology & Oceanography, Program and Abstracts, Jun. 16–20, 1996, Abstract—Toxicity and Environmental Sex Determination in *Daphnia Pulex*, University of Wisconsin–Milwaukee (1996).

Dodson and Hanazato, Abstract: Environmentally Induced Alterations in Development: A Focus on Wildlife, presentation to Wingspread Conference Center, Racine, WI (Dec. 1993).

S. Kilham and C. Goulden, handout entitled COMBO Medium (1995).

Dodson et al, Environmental Health Perspectives 103 (4);7–11, Commentary on Effects of Anthropogenic and Natural Organic Chemicals on Development, Swimming Behavior, and Reproduction of Daphnia, A Key Member of Aquatic Ecosystems (1995).

Baldwin et al. Environ. Toxicol. Chem. vol. 14, No. 6, pp. 945–952, 1995.

*Primary Examiner*—Leon B. Lankford, Jr.
*Assistant Examiner*—Christopher R. Tate
*Attorney, Agent, or Firm*—Godfrey & Kahn, S.C.

[57] ABSTRACT

The invention provides a 6-day Daphnia reproductive bioassay for detecting and confirming the presence of a toxic substance in an aqueous sample, and/or for screening the substance as an endocrine disrupter. According to the assay, a test sample is brought into contact with at least three adult, oviporous Daphnia of a single clone under conditions of crowding and suboptimal growth conditions to cause stress and stimulate sexual reproduction. The preferred clone for use in the assay is *Daphnia galeata-mendotae* Wingra clone CDF-1. The bioassay is based upon the measurement of five endpoints that convey quantitative information about the biological activity of the substance: survivorship, numbers of female offspring, numbers of male offspring, number of resting eggs, and number of offspring that display developmental deformities. Also provided are kits for use in conducting the bioassay.

19 Claims, 6 Drawing Sheets

FIG_1

FIG_2a

FIG_2b

FIG_2c

FIG_2d

FIG_3a

FIG_3b

FIG_3c

FIG_3d

FIG_3e

DAPHNIA REPRODUCTIVE BIOASSAY FOR TESTING TOXICITY OF AQUEOUS SAMPLES AND PRESENCE OF AN ENDOCRINE DISRUPTER

BACKGROUND OF INVENTION

In early toxicity tests of chemicals, the measured endpoint was acute toxicity. Over the past ten years, toxicity testing has expanded to include measures of sub-chronic toxicity including cancer, immune suppression, developmental effects and endocrine system disruption. Today, there is increasing concern about the long-term effects of anthropogenic chemicals such as polychlorinated biphenyls (PCBs), pesticides and plasticizers, among others, found in water, food, air and the materials around us. An increasing number of wildlife species are having reproductive difficulties, and there is current concern about declining sperm counts in human males.

Safe environmental concentrations of toxicants are those that allow humans and indigenous organisms in nature to complete their life cycles unimpaired. Toxicity tests that include exposure through the entire life cycle are the most useful tools for such measurements but can be too long and costly to be applied in most toxicity assessments. As a result, several short-term tests have been developed to estimate chronic toxicity, representing compromises of speed, sensitivity and cost. Most measurements of toxicity today rely on these short-term tests to indicate concentrations above which toxic effects are expected.

Daphnia are widely used in testing for aquatic toxins because of their rapid clonal reproduction, ecological importance, and sensitivity to their chemical environment. Toxicity tests using Daphnia have typically been used to detect changes in survivorship and fecundity.

Cladoceran zooplankton such as Daphnia can employ a reproductive strategy known as cyclical parthenogenesis in which one generation of sexual reproduction is interspersed with many generations of asexual reproduction. The ability to alternate life history strategy allows cladocerans such as Daphnia to achieve a high reproductive rate asexually when conditions are favorable, and to produce offspring sexually for survival when the environment becomes unsuitable. Under favorable environmental conditions, Daphnia reproduce asexually by producing eggs that hatch into female offspring that, in turn, asexually produce eggs that also hatch into female offspring, and so on. Populations can achieve high growth rates during the asexual phase as females mature in 8 to 11 days. The Daphnia population in Lake Mendota, Madison, Wis., is typically entirely female with occasional males and sexual females in late summer.

Sexual reproduction is initiated when females produce males and haploid resting eggs under conditions of stress such as crowding, food scarcity, low temperatures, short photoperiod, or chemical cues emitted by predators. Males mate with sexual females to produce resting eggs that can persist in a dormant state for years, allowing the population to survive hard times. Fertilized zygotes develop into embryos that enter diapause. These embryos are contained in a durable ephippium and can remain viable for years in sediments before hatching in response to environmental cues. Production of ephippia can be essential to maintain a Daphnia population in an environment that periodically becomes uninhabitable.

Bioassays that employ Daphnia are used to monitor and give a rough indication of the level of contamination in waters, and to test a specific chemical to predict the risk posed to biological communities. There are several standard assays that presently use Daphnia for measuring the toxicity of chemical substances in an aquatic sample. One such bioassay has been developed by the U.S. Environmental Protection Agency (EPA) to assess the relative toxicity of effluents and surface waters (U.S. EPA, "Short-term methods for estimating the chronic toxicity of effluents and receiving waters to freshwater organisms"(3d ed.), Section 13, Daphnid, *Ceriodaphnia dubia,* Survival and Reproduction Test, Method 1002.0, Lewis et al. (eds.), Environmental Monitoring Systems Laboratory, Cincinnati, Ohio (EPA/600/4-91/002, July 1994)). The EPA bioassay employs neonates (<24 hours old) of *Ceriodaphnia dubia* during a three-brood, 7-day static renewal test, with test results measured in terms of survival and reproduction.

Another bioassay that is currently used is a 21-day test provided by the American Society for Testing and Materials (ASTM) to examine the toxicity of a water sample or other material (ASTM Standards on Aquatic Toxicology and Hazard Evaluation, Standard Guide for Conducting Renewal Life-Cycle Toxicity Tests with *Daphnia magna,* Method E 1193-87, Philadelphia, Pa. (ASTM PCN 03-547093-16, May 1988). The ASTM Daphnia assay is labor-intensive and the organisms are grown at high food levels which involves regularly changing water to keep the organisms well fed and maximally reproducing. A single organism is placed into each of ten separate vials, the test is run for 21 days, and the endpoint measurement is the total number of surviving organisms. Under these conditions, the Daphnia reproduce female offspring by asexual reproduction.

A drawback of the EPA and ASTM Daphnia bioassays is that the assays only consider the effects on Daphnia during the asexual phase of their life cycle. In those bioassays, the animals are grown under conditions that optimize growth and asexual reproduction. However, projections of the species, community or ecosystem level risk posed by waterborne contaminants based on bioassays of asexual reproduction may ignore serious effects on reproductive strategy. Such bioassays can miss or make false predictions about the real effects of toxic chemicals in the environment because they do not measure toxic effects during a fundamental part of the life cycle of the model organism. Many invertebrates such as Daphnia with complex, multi-stage life histories may show variable sensitivity at different points in their development and over the course of an annual cycle. Toxicity can have entirely different consequences if it coincides with sub-optimal environmental factors. Effects that occur during crucial periods such as the sexual production of dormant stages, may have disproportionate consequences at the population level.

Other disadvantages of the EPA and ASTM assays are that they tend to provide inconsistent and highly variable, irreproducible results within and between laboratories, do not measure the effects of contaminants on production of males, and provide no information on sex ratio or on developmental changes.

Daphnia bioassays have been disclosed that subject the organism to stress to measure survivorship. See for example, U.S. Pat. Nos. 5,481,815 (Murphy) and 5,169,777 (Haley) which describe a 48-hour toxicity bioassay using *Daphnia magna* neonates. Drawbacks of such assays are that they measure only strong (e.g., acute) effects of a contaminant and fail to detect subtler effects that may be ecologically important, and give no information on male production or sex ratio or resting egg production. Anthropogenic chemicals interact with developmental pathways of many different animals, and invertebrates such as Daphnia which have alternate life history patterns may be susceptible to different chemical interactions during its two stages of reproduction. Such effects would not be detected in a 48-hour bioassay. Furthermore, a 48-hour bioassay would not detect the consequences of toxic effects on sexual reproduction of Daphnia which can appear in depressed hatching of resting eggs.

Many pesticides, toxic xenobiotics such as some PCBs and dioxins, and common industrial chemicals such as nonylphenol and phthalates, affect and disrupt the endocrine system of an animal (i.e., endocrine disrupter). Such chemical substances can function as estrogen mimics and are implicated as agents that interfere with male development in wildlife populations such as alligators, sea gulls, turtles, salmon and trout. Endocrine disrupters effect the life history of Daphnia to trigger or suppress the production of males and resting eggs, and/or cause visible developmental deformities in the offspring. For example, low levels of the plasticizer nonylphenol have been shown to reduce resting egg production, and cause a characteristic deformity by preventing normal development from the embryo to the neonate stage. However, there is no bioassay currently available to quickly and reliably test for the presence of endocrine disrupters in a water sample.

Accordingly, an object of the invention is to provide a bioassay that is relatively easy to perform, fast, highly accurate and sensitive, and provides ecologically meaningful test information to evaluate environmental toxicity. Another object is to provide a test assay that is highly consistent within and between laboratories, and is easy to perform. Another object is to provide a bioassay and test kit for detecting toxic substances in a sample and to relate such toxicity to a particular type of chemical agent. Yet another object is to provide a bioassay that can be used to detect the presence of an endocrine disrupter, including estrogen mimics, in a water sample, and to test the activity of a chemical substance for activity as an endocrine disrupter.

SUMMARY OF THE INVENTION

These and other objects are achieved by the present invention which is directed to a 6-day Daphnia reproductive bioassay for use in assaying an aqueous sample for toxic substances and identifying the nature of the toxin as a substance that can affect the endocrine system of an animal (i.e., endocrine disrupter), and to test a chemical substance for biological activity as an endocrine disrupter. Also provided are kits for use in conducting the bioassays.

The present Daphnia reproductive bioassay for toxicity examines the effects of biologically active chemicals in terms of life history features that include survivorship and mortality, fecundity, male:female sex ratio, and observed deformities in offspring. The bioassay is conducted under conditions in which sexual reproduction will occur, and the reduction or enhancement of sexual reproduction in the test sample is then compared to a control to determine the deviation from normal sexual reproduction in the control.

The 6-day assay involves growing at least three adult, oviporous Daphnia of a single clone together in a small volume of water. These "crowded" conditions, optionally along with limited food levels, short day length (long night) and/or relatively cool temperature, act together to provide conditions by which the Daphnia will produce both male and female offspring. These "control" conditions are optimal for producing males while maintaining fecundity and survivorship. The control conditions are suboptimal for producing maximum fecundity. Thus, the animals are somewhat stressed (as they are often in nature) by the control conditions and more likely to respond to very low but ecologically important levels of toxic chemicals in the test treatments.

The bioassay is useful for testing and screening an aqueous sample for the presence of a toxic substance and/or a substance that can effect the endocrine function of an animal. For example, the bioassay can be used for testing for the presence of an herbicide, insecticide, fungicide, xenobiotic, plasticizer, phytohormone, phytoestrogen, and the like. The assay is conducted by preparing a control, and a test sample that contains an aliquot of a sample to be tested in an aqueous medium (i.e., water sample, industrial effluent, elutriate of soil, and the like) combined with an amount of a Daphnia minimal growth medium, to achieve a condition of crowding of Daphnia in the contained test sample and control. A change in the numbers and proportions of males, females and resting eggs indicates the presence of a toxic substance in the test sample. After an initial screening, the substance in the test sample can be further identified according to known assays and testing methods that can also be used to confirm the presence of an endocrine disrupting substance in the sample.

The present Daphnia reproduction bioassay is also useful as an initial screening to test the activity of a known or unknown substance for its biological effect on the endocrine function of an animal. In such a bioassay, a test sample and a control can be prepared as an aqueous dilution of the substance to be tested in a Daphnia minimal growth medium to achieve crowding of Daphnia.

In the present bioassay assay, at least three (3) female adults of a single clone of Daphnia are added to the test sample, and the test sample and the control are maintained under suboptimal growth conditions of temperature (preferably about 20° C.) and photoperiod (preferably 9:15 hours light:dark) for Daphnia for a 6-day period. The preferred clone for use in the present assay is derived from *Daphnia galeata-mendotae*, with Wingra clone CDF-1 being preferred.

The bioassay is based upon the measurement of five endpoints that convey quantitative information about biologically active chemicals in an aqueous sample. These endpoints include: survivorship of adult females, survival of male and female neonates (newly-born offspring), total numbers of offspring, male:female sex ratio, and number of resting eggs. At the end of the 6-day test period, the five endpoints are measured and comparisons are drawn between the test sample and the control.

Daphnia undergoes sexual reproduction in response to environmental stress. The ratio of male to female offspring and the number of resting eggs (ephippia) indicate the level of stress to which the animal is exposed. Differences in these values between control animals and those exposed to a test sample indicate the presence of toxic substances, and potentially the presence of substances which interfere with endocrine processes.

To assure that the assay is conducted under optimal conditions, the controls are examined to confirm, on average, a zero to low mortality, a high male:female sex ratio with a proper proportion of males at about 30–70% of the total offspring, and a lack of resting eggs. The presence of an endocrine disrupter substance is indicated by a significant variance or statistical difference between the test sample and the control of the male:female sex ratio, the number of resting eggs, and/or neonates with a morphological abnormality. An endocrine disrupter substance in the test sample is particularly indicated by a change or variance relative to the control in a male:female sex ratio that is statistically higher or lower than the control, an increase in resting eggs, and offspring with a developmental deformity.

The invention further provides a kit for conducting the bioassay. The kit can include containers, a device for manipulating the Daphnia test organisms, cultures of a Daphnia clone and/or algal food species, and instructional materials for culturing the Daphnia and algae, for conducting the assay and scoring the results, and other like materials for conducting a bioassay.

The present Daphnia bioassay can be used to quickly assay an aquatic sample for the presence of a toxic substance and indicate the presence of a potential endocrine disrupter, and to test a substance for activity as an endocrine disrupter. The present 6-day bioassay is superior to other methods of biotesting for toxic effects of chemicals dissolved in water, at least in part because it measures the effects of potential toxicants on developmental integrity, sex ratio and resting egg production as well as survivorship and fecundity. These additional endpoints are more informative and sensitive endpoints than survival and fecundity. The present Daphnia reproductive bioassay provides an indication of hormone-like chemical toxins in water that are ecologically important but may not reduce either short-term fecundity or survivorship. In addition, the Daphnia reproductive bioassay provides an insight into the mechanism or toxicity, where other assays only indicate the presence or absence of toxicity. The information generated from the present bioassay may also reduce the need for expensive chemical analysis, thereby reducing overall costs in monitoring.

The Daphnia reproductive bioassay of the present invention is useful in biomonitoring laboratories of the federal and state government, and private laboratories such as those of large chemical companies. The assay can be used to (1) evaluate the toxic effects of individual chemical formulations for product testing as required by the Food and Drug Administration (FDA), (2) for pesticide registration as required by the U.S. Department of Agriculture (USDA), and (3) to screen natural waters or effluents from industry or municipalities for toxic potential for mandated testing required by programs of the Environmental Protection Agency (EPA) such as the National Pollutant Discharge Effluent, Superfund, and the Resource Conservation and Reclamation Act programs.

DETAILED DESCRIPTION OF THE INVENTION

The present Daphnia reproductive bioassay examines not only toxicity of chemical substances in a test sample but also the mechanism that underlies the physiological stresses on reproduction, development and growth resulting from the toxic effect. The assay can be used to detect and confirm the presence of sublethal levels of a toxic chemical in an aqueous sample, and to indicate the nature of the chemical as a substance that can affect the endocrine system of an animal (i.e., an endocrine disrupter). The assay can also be used to screen a substance for activity as an endocrine disrupter.

The 6-day assay uses a clone of the freshwater cladoceran Daphnia (water flea) grown under defined, standardized conditions that cause the Daphnia to produce both male and female offspring. By comparison, in conventional, standard Daphnia bioassays of toxicity only female offspring are produced given the environmental conditions that are used. The present assay uses production, survival and gender of the Daphnia clone under controlled conditions, and involves measuring five (5) endpoints that convey quantitative information about a biologically-active agent in the sample. The endpoints that are measured are: 1) survivorship of adult females, 2) survival of male and female neonates (newly-born offspring), 3) total numbers of offspring, 4) male:female sex ratio, and 5) number of resting eggs. The present Daphnia reproductive assay requires male production in the control so that comparison of sex ratio with animals grown in test samples illuminates the biological activity of the toxin.

A preferred experimental unit is a small jar or other like container with about 30-ml of a growth medium for the Daphnia and at least three (3) adult egg-carrying female clone mates of a Daphnia clone, preferably 3–7, more preferably 4–6, more preferably 5 adult females per 30-ml growth medium. Containing 3–7 Daphnia into about 30-ml of medium facilitates crowding and the production of male offspring.

Suitable Daphnia clones for the Daphnia reproductive assay are characterized by: (1) low mortality in the control treatment (the standard EPA criterion is less than 20% mortality); (2) consistent performance (reproduction and development) in control conditions; (3) ease of handling; (4) avoidance of the growth medium surface film in the experimental jars; (5) reliable reproduction; (6) production of males; and (7) production of resting eggs under stressful conditions.

Daphnia clones can vary in their reproductive strategy and not all Daphnia clones produce males or resting eggs. Daphnia clones suitable for use in the assay can be screened by running the 6-day bioassay under control conditions (e.g., 30-ml growth medium, 3–7 adult clones, 20° C., a 9:15 hour light:dark ratio, and medium renewal after 3 days. A preferred Daphnia clone is one that will consistently and repeatedly produce about 30–70% males of the total number of offspring in repetitive tests under control conditions of the same growth medium, algal food source, temperature, test period, photoperiod, pH, and medium renewal.

The *Daphnia galeata mendotae* Wingra CDF-1 clone has been found to consistently produce about 15–50% males under such environmental conditions, and is available by contacting the University of Wisconsin-Madison, Attn: Dr. Stanley Dodson, Department of Zoology, Birge Hall, Madison, Wis. U.S.A. 57306. Other Daphnia clones that were screened and found to produce a lower percent of males include, for example, *Daphnia galeata mendotae* Oneida clone, and *Daphnia pulex* clones K, SBL and 9A-25 (Innes). Daphnia clones that were found to produce ephippia, such as *Daphnia hyalina* Stich clone, *Daphnia lumholtzi* Texas clone and *Daphnia pulex* clone A, are also useful in the bioassay.

The growth medium in the assay is used to culture both the algal food source for the Daphnia and the Daphnia test clone itself. The growth medium includes an effective level of nutrient salts to grow algae but not interfere with normal growth and development of Daphnia.

The growth medium also contains an initial level of algae (food) that is sufficient to maintain Daphnia survival and reproduction during the test period. A preferred food source is an about 1:1 mixture of two green algae, *Chlamydomonas reinhardti* and *Selenastrum capricomutum*. These algae are commercially available from the Culture Collection & Algae, Department of Botany, University of Texas at Austin, Austin, Tex. 78713-7640. The algal mixture is provided at an initial level of about $5 \times 10^5$ cells per ml, which is about 6.9 mg carbon per ml. The algae are allowed to settle out between changes of the medium every three (3) days. Other algae that may be used as the food source include *Selenastrum minitum, Ankistrodesmus convolustrus,* and *A. falcatus,* and the like, optionally with a diatom such as *Nitschia frustulum* as a dietary supplement.

A preferred growth medium is an artificial lake water medium developed by S. Kilham and C. Goulden (personal communication), as described in EXAMPLE 1. Experimental units of the Daphnia reproductive bioassay are placed for incubation into an environmentally-controlled chamber with photoperiod and temperature control and with light levels at a maximum of about 500 uE per meter squared per second. The growth medium is preferably changed on day 3–4 of the assay by pipetting the adult Daphnia into new containers of 30-ml of growth medium and algae. Any neonates produced during the first 3 days are discarded. After an additional 3 days, the neonates and adults are scored for the five endpoints.

The assay is run with "controls" and "treatments" (test samples). In a preferred set-up, the control conditions are as follows: 30 ml growth medium (with no added chemical or suspect water), 3–7 adult Daphnia; temperature of about 20° C.; photoperiod of 9 hours light and 15 hours darkness; one medium renewal after 3 days; and 6-day total duration of the assay. Under such conditions, the oxygen concentration will remain above about 5 mg per liter without aeration. The medium can also be aerated to increase the dissolved oxygen (DO) to a level of at least about 4 ppm.

A "treatment" or test sample uses the same conditions as the control, with the addition of a test sample to the growth medium. In a preferred set-up, the control and treatments are replicated to provide multiple jars (experimental units) for each control or treatment, for example 12–15 units. In testing a water sample or substance for bioactivity, it is also advantageous to run the test sample as serial dilutions of the chemical substance or aqueous sample to provide a range of concentrations, e.g. 10, 50, 100, 200, 400 $\mu$g per liter, particularly in the case of high levels of toxicity. The bioassay can also be designed to detect sublethal effects of the chemical or substance such as a change in sex ratio by preparing the test sample as a series of dilutions of the substance to provide concentrations that do not affect the survival of adult Daphnia. It is also advantageous to screen effluent and surface and ground waters by running the bioassay at 100% sample (with added growth medium) to compare to controls (growth medium only).

To score the Daphnia at the end of the bioassay, the 30-ml of growth medium and Daphnia can be poured into a 30-ml plastic petri dish or other like container. The water is removed, for example, using a large-bore pipette whose opening is covered with 120 $\mu$m nylon mesh. A smaller pipette, similarly covered with mesh, can be conveniently used to remove remaining water so that the Daphnia are caught in the surface film of a thin layer of water remaining in the petri dish or other container. Each time a pipette is used, care should be taken to avoid trapping Daphnia on the mesh, for example, by placing a drop of water back into the petri dish. The petri dish or other container can be moved to a dissecting microscope and the entire surface is scanned for living and dead Daphnia. This procedure can be repeated for each jar or container (experimental unit). Results can be recorded on a score sheet, including data on the date, time, number of resting eggs, and number, condition, stage and gender of the observed Daphnia. The bioassay can further include conducting a chemical assay or other additional assay as known and used in the art to confirm the identity of a substance and/or the activity of the substance as an endocrine disrupting substance.

Males and females are distinguished by the shape of the rostrum (long and pointed in females, short and rounded in males), and the length of the first antennae (shorter than the rostrum in females, longer than the rostrum in males). Resting eggs are distinguished from normal ("subitaneous") eggs by pigmentation (resting eggs are opaque and black or brown, compared to the mostly clear normal eggs). Resting eggs are held in thickened and black brood chamber, while normal eggs lie in a transparent brood chamber.

Offspring are examined for gross and visible morphological abnormalities while they are scored for gender. Such deformities indicate a teratogenic effect and interference of a chemical substance during early development. Abnormalities include, for example, reduced or absent terminal setae on the second antennae (swimming appendages), short or blunt or forward-curved tail spine, rounded helmet, and/or a missing eye.

Samples that can be tested by the Daphnia reproductive bioassays can be taken, for example, from a natural water source such as a river, natural lake, municipal water supply lake, domestic drinking (tap) water, storm water, ground water, an industrial effluent, municipal effluent, or sewage influent or effluent, or a synthetic testing medium as in the case of product testing. The test sample can also be an extract or elutriate from solid samples such as, for example, soil, aquatic sediment, sludge, wood, plant material, paper or pulp. The solid sample can be extracted with the growth medium for about 12 hours or other suitable time period; centrifuged, and the elutriate then tested.

Examples of toxic substances that are known or potential endocrine disrupters that can be detected using the present bioassay include: herbicides such as dicamba, atrizine and other triazines; insecticides such as dieldrin, endosulfan, chlorpyrifos, pentachlorophenol (PCP), and dichlorodiphenyltrichloroethane (DDT); phytohormones such as coumestrol; mycotoxins such as zearalenone and zearalenol; artificial hormones such as diethylstilbestrol (DES); industrial chemicals such as plasticizers, surfactants and residues thereof, nonylphenol and related alkylphenols, and phthalates; drugs such as tetrahydrocannabinol; food additives such as colorings and preservatives; natural toxins produced by cyanobacteria such as *Microcystis aerugenosa;* organic solvents such as ethanol; and the like. Examples of estrogen-mimicking compounds that are known or potential endocrine disrupters include estradiol, DES, kepone (chlordecone), DDT, dichlorodiphenyldichloroethane (DDD), 1-hydroxychlordene, chlordane, zearalenone, coumestrol, nonylphenol, butylphenol, pentylphenol, isopentylphenol, polychlorinated biphenyl (PCB), chlorpyrifos, PCP, atrazine, carbaryl, endosulfan, or derivatives thereof (See, Colborn et al., "Developmental Effects of Endocrine-Disrupting Chemicals in Wildlife and Humans," *Environmental and Health Perspectives* 101 (5): 378–384 (1993)).

The presence of a toxic substance in a test sample (overt toxicity) is indicated by one or more of the following parameters, based on a statistical analysis:

1. significantly ($\alpha=0.05$) lower survivorship of adults in the treatment (test sample) compared to the survivorship of adults in the control (which should be at least about 80% over six days);

2. significantly fewer neonates produced in the treatment compared to the control fecundity; and/or 3. significantly fewer neonates surviving in the treatment (indicated by the number of dead neonates observed at the end of the six day test period) compared to the survivorship of neonates in the control.

The presence of an endocrine disrupter is indicated by one or more of the following parameters (which may occur without any of the above-listed parameters that indicate overt toxicity):

1. significant increase or decrease in the sex ratio in the treatment compared to the control;

2. significant increase in the number of resting eggs in the treatment compared to the near zero number of resting eggs in the control; and/or 3. significant increase in number of morphological abnormalities in the treatment compared to the near zero abnormalities in the control.

The bioassay can be provided in kit form that includes, in association, for example, containers for the test sample(s) and controls; a pipette or other like device for manipulating the Daphnia (test organisms); a shallow glass dish or other like container for observing the Daphnia, a starter culture of a Daphnia clone as the test organism; directions for Daphnia culture; a starter culture of algal food species; directions for culturing the algae; a growth medium for culturing the Daphnia and/or the algae; directions for setting up and performing the bioassay; directions for scoring the results of test and model data scoring sheet; directions for statistical analysis of the results; software for data analysis; instructional video; and information on standard responses of the Daphnia to known endocrine disrupters. The parts of the kit can be contained or separately packaged, for example, in a box or bag, and sold and distributed to users. The directions can be provided as a paper copy or on computer disk.

The invention will be further described by reference to the following detailed examples, wherein the methodologies are described below. These examples are not meant to limit the scope of the invention that has been set forth in the foregoing description. Variation within the concepts of the invention are apparent to those skilled in the art. The disclosures of the cited references throughout the application are incorporated by reference herein.

EXAMPLE 1

Minimal Growth Medium

The test sample(s) and control include a growth medium to provide minimal amounts of nutrients and trace elements and an algae food source for supporting the Daphnia neonates and offspring during the 6-day test period.

It is preferred that the growth medium is changed every 3 days during the 6-day test period in order to maintain sufficient food and oxygen concentrations, to remove neonates that began their development before the assay began (developmental time of the Daphnia eggs in the brood chamber is about 2.5 days), and to insure that the neonates scored at the end of the bioassay experienced their full development in the control and treatment solutions. It is also desirable to monitor the pH, conductivity and dissolved oxygen (DO) when the medium is changed to assure consistent conditions throughout the test period.

A preferred growth medium is that developed by S. Kilham and C. Goulden (personal communication) which is prepared as follows. For one (1) liter of minimal growth medium, 1-ml of each of the Seven Major Stock Solutions, 1-ml of Algae Trace Elements Master Stock, 1-ml of Animal Trace Elements Master Stock, and 0.5 ml of Vitamin Master Stock are combined, and brought to a final volume of one (1) liter.

Seven Major Stock Solutions. The following 7 major stock solutions are prepared separately by combining the listed salt in one (1) liter distilled water. The stock solutions are stored at room temperature):

| | | | |
|---|---|---|---|
| 1) $CaCl_2.2H_2O$ | 36.76 g | calcium chloride dihydrate |
| 2) $MgSO_4.7H_2O$ | 36.97 g | magnesium sulfate heptahydrate |
| 3) $K_2HPO_4$ | 8.71 g | potassium phosphate dibasic anhydrous |
| 4) $NaNO_3$ | 85.01 g | sodium nitrate |
| 5) $NaHCO_3$ | 12.60 g | sodium bicarbonate |
| 6) $Na_2SIO_3.9H_2O$ | 24.42 g | sodium metasilicate nonahydrate |
| 7) $H_3BO_3$ | 24.0 g | boric acid |

Algae Trace Elements Stock Solution. Mini stock solutions, each 100-ml in total volume, are prepared separately to contain one of the following salts. The solutions are refrigerated).

| | | |
|---|---|---|
| 1) $MnCl_2.4H_2O$ | 18.0 g | manganese(II) chloride tetrahydrate |
| 2) $CuSO_4.5H_2O$ | 0.1 g | copper(II) sulfate pentahydrate |
| 3) $ZnSO_4$ | 2.2 g | zinc sulfate heptahydrate |
| 4) $CoCl_2.6H_2O$ | 1.0 g | cobalt(II) chloride hexahydrate |
| 5) $Na_2MoO_4.2H_2O$ | 2.2 g | sodium molybdate dihydrate |
| 6) $H_2SeO_3$ | 0.16 g | selenious acid |
| 7) $Na_3VO_4$ | 0.18 g | sodium orthovanadate |

One (1) liter of Algae Trace Elements Master Stock Solution is prepared by combining the following ingredients. The EDTA is dissolved first to avoid formation of an insoluble precipitant:

| | | |
|---|---|---|
| 1) $Na_2EDTA.2H_2O$ | 4.36 g | ethylenediaminetraacetic acid, disodium salt dihydrate |
| 2) $FeCl_3.6H_2O$ | 1.0 g | iron (III) chloride hexahydrate |
| 3) 1-ml of each of the mini stock solutions (1–7). | | |

Animal Trace Elements. Mini stock solutions, each 100-ml in total volume, are prepared separately to contain one of the following salts. The solutions are refrigerated). One (1) liter of Animal Trace Elements Master Stock Solution is prepared by combining 1-ml of each of the mini stock solutions.

| | | |
|---|---|---|
| 1) LiCl | 31 g | lithium chloride anhydrous |
| 2) RbCl | 7 g | rubidium chloride |
| 3) $SrCl_2.6H_2O$ | 15 g | strontium chloride hexahydrate |
| 4) NaBr | 1.6 g | sodium bromide |
| 5) KI | 0.33 g | potassium iodide |

Vitamins Stock Solution. Mini stock solutions are prepared for the following two vitamins. The solutions are kept sterile and frozen:

1) biotin dissolve 10 mg in 96-ml of $H_2O$

2) $B_{12}$ dissolve 10 mg in 89-ml of $H_2O$

A Vitamin Master Stock Solution of 100-ml total volume is prepared by adding 1-ml of each of the biotin and $B_{12}$ stock solutions, and 20-mg thiamine. The master stock solution is dispensed into 10-ml lots and autoclaved or microwaved.

EXAMPLE 2

Bioassay of Two Pesticides for Activity as an Endocrine Disrupter

Two widely used contemporary pesticides, dieldrin and endosulfan, were tested for activity as endocrine disrupters using the present Daphnia reproduction bioassay.

Levels of exposure of the pesticides were chosen based on reports of results of standard bioassays (for fecundity and survivorship) in the literature. Concentrations were chosen that were at or below levels known to have toxic effects in Daphnia or other freshwater species. Concentrations of 10 and 100 μg per liter of each pesticide alone, and a mixture of the two pesticides, both at either 10 and 100 μg per liter.

The bioassay was performed as follows. The experimental unit was a glass jar containing 30-ml of the growth medium described in EXAMPLE 1 above, and a 1:1 mixture of the green algae, *Chlamydomonas reinhardti* and *Selenastrum capicornutum* (Culture Collection & Algae, Department of Botany, University of Texas at Austin, Austin, Tex. 78713-7640) which provided the algal mixture at an initial level of about 5×105 cells per ml (about 6.9 mg carbon per ml). Into each jar were placed three (3) adult egg-carrying female *Daphnia galeata mendotae* Wingra CDF-1 clone (University of Wisconsin-Madison, Department of Zoology). The Daphnia were incubated in an environmentally-controlled chamber for three (3) days at 20° C. and 9 hours of light (500 μE per meter squared per second (maximum)) per day. Each jar contained growth medium with or without additional chemical, as shown below. Each Control or treatment was replicated 15 times.

Controls:
  Control: Growth medium, algae
  Acetone Control: Growth medium, algae, 200 mg/L Acetone Treatments: Growth medium, algae, plus:
  Low Dieldrin Treatment: 10 μg/l Dieldrin
  Low Endosulfan Treatment: 10 μg/l Endosulfan
  Low Mixture: 10 μg/l Dieldrin, 10 μg/l Endosulfan
  High Dieldrin Treatment: 100 μg/l Dieldrin
  High Endosulfan Treatment: 100 μg/l Dieldrin
  High Mixture: 100 μg/l Dieldrin and 100 μg/l Endosulfan At the end of three (3) days, the adults were pipetted into new jars containing 30-ml of fresh growth medium and algae food source, and any neonates were discarded. After another three (3) days, the neonates and adults in the bottle were counted and scored for survivorship, resting eggs, and gender.

Results of the experiments with low concentrations of pesticides showed no difference in survivorship, fecundity, resting eggs, or gender between the two controls or between the controls and any of the treatments.

Results of the experiments with low levels of pesticides are shown below in Table 1.

TABLE 1

| TREATMENT | NUMBER OF FEMALES | NUMBER OF MALES |
|---|---|---|
| Control | 146 | 18 |
| Acetone Control | 143 | 17 |
| Low Dieldrin | 144 | 21 |
| Low Endosulfan | 151 | 22 |
| Low Dieldrin and Low Endosulfan | 132 | 21 |

Results of the experiments with high levels of pesticides for the first clutch are shown below in Table 2.

TABLE 2

| TREATMENTS | NUMBER OF FEMALES | NUMBER OF MALES |
|---|---|---|
| Control | | |
| Acetone Control | 114 | 13 |
| High Dieldrin | | |
| High Endosulfan | | |
| High Dieldrin and High Endosulfan | 65 (10 replicates) | 14 |

Figure 1:
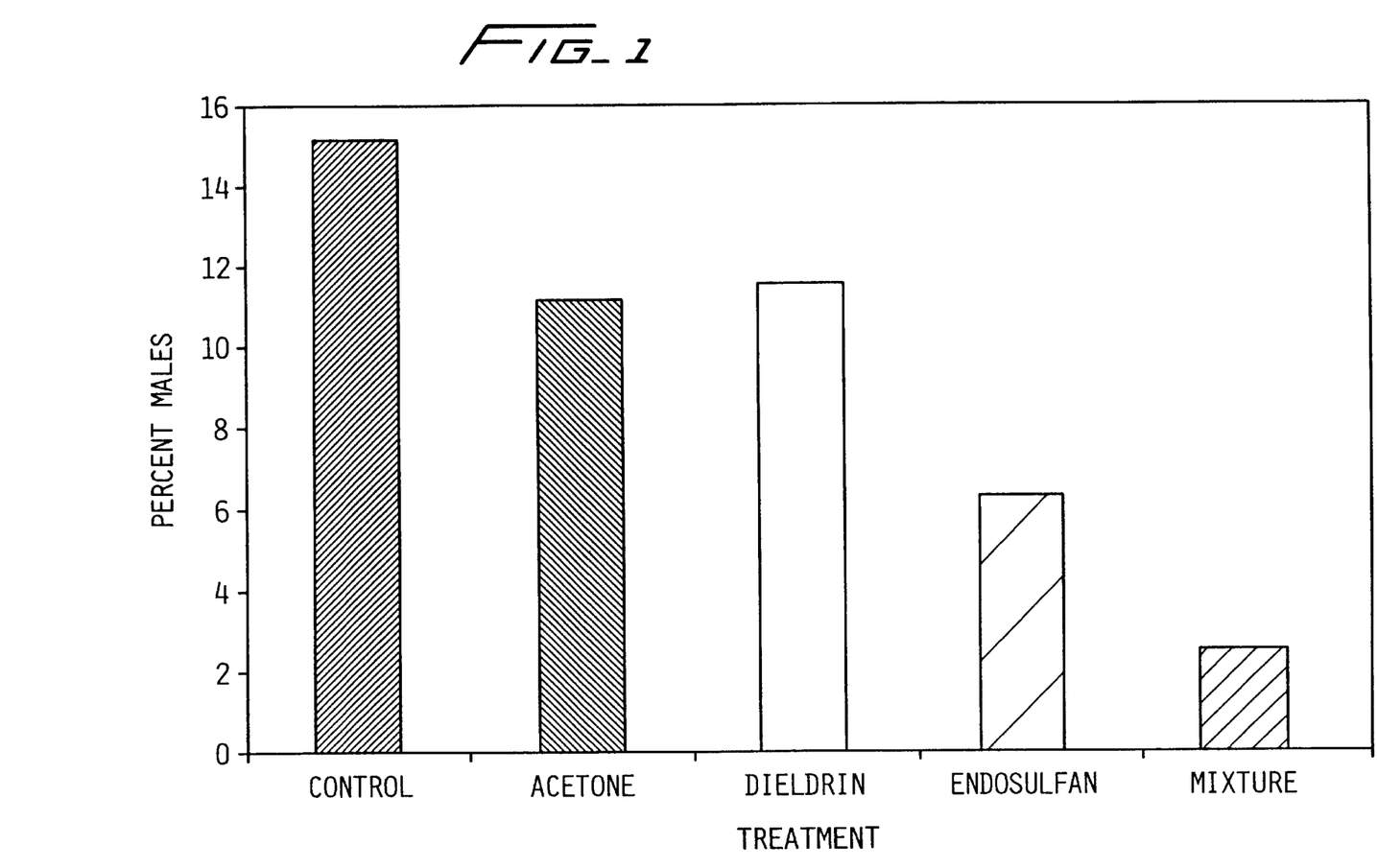
FIG. 1 is a graphical comparison of the effects of 100 $\mu$g per liter of two pesticides, dieldrin and endosulfan.

Results of the experiments with high levels of pesticides for the second clutch are shown below in Table 3, and illustrated in FIG. 1.

TABLE 3

| TREATMENTS | NUMBER OF FEMALES | NUMBER OF MALES |
|---|---|---|
| Control | 118 | 18 |
| Acetone Control | 116 | 13 |
| High Dieldrin | 120 | 14 |
| High Endosulfan | 126 | 8 |
| High Dieldrin and High Endosulfan | 121 | 3 |

The results of the experiments with high level of pesticides showed no difference between the two controls, no difference between the controls and the dieldrin treatment, a tendency for a reduction of males in the endosulfan treatment but no other changes, a strong reduction in sex ratio (few males) in the mixture, and a slight (not significant) adult mortality (12%). These results indicate that endocrine disruption occurred at levels below those that are lethal or even affect fecundity or survivorship, and a synergistic interaction of the two pesticides.

EXAMPLE 3

Method and Protocol for Daphnia Reproductive Bioassay for Testing an Aqueous Sample To test a water sample for a biologically-active level of a toxic chemical and/or the presence of a chemical substance that functions as an endocrine disrupter, the Daphnia reproductive bioassay can be run as follows.

A series of test sample and control experimental units can be prepared and the bioassay run under the conditions described in EXAMPLE 2. The control and test samples can be replicated so there are multiple units that are assayed for each. The unknown water sample can also be run as serial dilutions by adding a range of amounts of the water sample to the growth medium, for example from 1–15 ml of the water sample with 0.9–15 ml growth medium. The control is made with the minimal growth medium but with no added water sample.

After three (3) days, the adults are transferred to fresh growth medium and the neonates removed. After an additional three days, the neonates and adults in each experimental unit are scored for survivorship, resting eggs and gender, and the 5 parameters scored and compared between test samples and control.

EXAMPLE 4

Sublethal Toxic Effects of Cyanobacteria and Nonylphenol on Environmental Sex Determination and Development in Daphnia The effects of toxic stress were studied on *Daphnia galeata-mendotae* grown under conditions in which the organism produces female, male and ephippial offspring (Shurin, J. and S. I. Dodson, "Sublethal toxic effects of Cyanobacteria and nonylphenol on environmental sex determination and development in Daphnia," *SETAC Journal* (in press, 1997)). The bioassay used was a 21-day protocol that started with Daphnia neonates. Fecundities in terms of three (3) types of offspring showed different sensitivities to chemical stress. The toxic agents were a natural toxin produced by a toxic strain of the cyanobacterium *Microcystis aeruginosa*, and an anthropogenic toxin, a chemical plasticizer nonylphenol which is a surfactant that interferes with endocrine function in vertebrates.

Production of resting egg and female offspring were affected in both cases, but showed different dose responses. Exposure to nonylphenol also produced a characteristic developmental abnormality at environmentally relevant concentrations. Some neonates that were prenatally exposed to toxins showed signs of incomplete morphological transition from embryo to juvenile. Life table analysis showed stress during the sexual phase of Daphnia's life cycle reduced population growth.

The cyanobacterium, *Microcystis aeruginosa* produces chemical defenses against grazing by herbivorous zooplankton and often forms large toxic blooms especially in eutrophic lakes. Microcystis suppresses growth and reproduction of grazers in three ways: by producing toxins, by forming gelatinous aggregates that interfere with filtering appendages, and by providing low nutritive value.

Nonylphenol is a prevalent surfactant in sewage effluents. Nonylphenol and its ethoxylate derivatives have been detected at levels up to 330 and 419 $\mu gL^{-1}$ in British and Swedish waste waters respectively, and at 1.3 to 180 $\mu gL^{-1}$ in river waters in the same studies. Chronic $LC_{50}$ values for *D. magna* of 120, 120 and 100 $\mu gL^{-1}$ have been found in 7-, 14- and 21-day tests, respectively. Concentrations in waters show considerable variation in time and space, indicating that nonylphenol can be rare but present at biologically significant levels. Nonylphenol bioaccumulates in tissues, so effective exposure levels increase with time of contact. Nonylphenol and its derivatives have been shown to be estrogenic to fish, mammals and birds.

Life table analysis. Data from the Microcystis and nonylphenol experiments were analyzed to determine the consequences for short-term population dynamics of chemical stress on Daphnia in the initial stage of sexual reproduction. The instantaneous rate of population increase (r) was estimated for experimental animals grown at different levels of toxic stress. The rate of increase is a measure of the growth rate of the population of live, pelagic females available for immediate sexual or asexual reproduction. It is a function of survival and fecundity of animals of different age classes. Toxins that affect r can influence population dynamics over multiple generations, even if actual exposure takes place during only one generation. The rate of increase only considers present production of female animals and does not take into account multi-generational effects that may occur from reduced ephippia production.

Methods

General Methods for Bioassay. The animals used were a single clone (CDF-1) of *Daphnia galeata-mendotae* collected from Lake Wingra, Wis., USA by Thomas O'Keefe in December, 1994. This clone produces female, male and ephippial offspring when crowded. Several generations were grown in the lab before the experiment. Pairs of neonates (<36 hours old) were placed into 30-ml of medium at the beginning of the study. Animals were grown in pairs to provide crowding as a stimulus for the production of males and ephippia. The experiment began with sixteen replicate jars, and jars were discarded if either animal died.

The medium was changed and the containers rinsed with distilled water every 2 days. Male, female and ephippial offspring were counted by visual inspection (at 25×) on days when the medium was changed and any mortality among the parental Daphnia was recorded. The medium in which the algae and zooplankton were cultured was the combination formula as described hereinabove in EXAMPLE 1. This formula eliminates the problem of mineral rich algal culture medium causing unwanted effects on Daphnia. The zooplankton medium was kept under constant vigorous aeration before being used. Animals were grown in an environmental chamber at 20° C. with a constant 9:15 hour light:dark photoperiod. These conditions are similar to those during fall in Wisconsin when *Daphnia galeata-mendotae* undergo sexual reproduction.

Microcystis experiment. Semi-continuous cultures of the green alga *Chlamydomonas rheinhardii* (UTEX 90) and the cyanobacterium *Microcystis aeruginosa* (UTEX LB 2385) in log-phase growth provided food for zooplankton. Treatment levels were four ratios (by total particulate carbon content) of Microcystis: Chlamydomonas: 0:1, 1:9, 1:3, and 1:1. The strain of Microcystis that was used produces the toxin microcystin.

Animals were fed a total of 0.6 mg $C-L^{-1}$ (in particulate organic carbon) at the beginning of the experiment. After low reproduction in the first clutch, the food was increased to 1.0 mg $C-L^{-1}$ on the 10th day. Algae were added to the zooplankton medium immediately before the medium was introduced into the experimental containers. Concentrations of cells in the algae cultures were determined spectroscopically from standardized absorption curves. Carbon content of Microcystis was determined as described by W. Lampert, "Inhibitory and toxic effects of blue-green algae on Daphnia", *Int. Revue ges Hydrobiol.* 66(3):285–298 (1981). The containers were gently agitated on the days when the medium was not changed to resuspend any algal cells that had settled. The experiment was ended after 36 days.

Nonylphenol Experiment. Medium and growing conditions were the same as in the Microcystis experiment. Animals were fed 1 mg $C-L^{-1}$ Chlamydomonas which was increased to 1.2 mg $C-L^{-1}$ on the 6th day of the experiment because of poor growth. Three concentrations of nonylphenol were tested, 10, 50 and 100 $\mu g-L^{-1}$. In a preliminary experiment 100% mortality among animals was observed at 150 $\mu g-L^{-1}$ over 48 hours. Nonylphenol was dissolved in an acetone carrier to enhance its solubility in water. Carrier effects were tested by running controls with and without acetone. In the acetone control and in all the nonylphenol treatments, the acetone concentration was kept constant at 80 µg-L$^{-1}$. Stock solutions of chemicals for each treatment were kept refrigerated and added to the zooplankton medium immediately before it was used in the experimental containers. The experiment was ended after 30 days because of low survival in the 100 µg-L$^{-1}$ nonylphenol treatment and reduced reproduction in all treatments.

Some five offspring in the nonylphenol treatments showed developmental abnormalities. These offspring were approximately the same size as normal young but had forward-curled tail spines (a characteristic of Daphnia in embryonic stages) and lacked or had severely reduced terminal setae on their second antennae. These setae are used for swimming and deformed animals were unable to move or attempt to escape capture by a pipette. Offspring were considered to be deformed if they exhibited both a bent tail spine and reduced or absent terminal setae. All deformed offspring were assumed to be inviable and were not included in estimates of r. Deformed young were counted in calculating production of male and female offspring. Deformed offspring were not observed in the medium or solvent controls or in the Microcystis experiment.

Life table analysis. The average instantaneous rate of increase (r) and confidence intervals were calculated for each treatment by the Jackknife method described by Meyer et al., *Ecology* 67(5):1156–1166 (1986), and the Jackknife pseudovalues were included in the statistical analysis. All jars initiated at the beginning of the experiment were included in estimates of r. When an animal died, its partner in the jar was removed from the pool used to calculate the survivorship function ($l_x$). This was done by subtracting one animal (the dead Daphnia) from the number surviving on the day that the animal died. The other animal (the survivor) was subtracted from the total number possible (the denominator in $l_x$) on the next sampling point two days later. This correction prevented mortality estimates from being inflated by animals that were discarded but did not die.

Statistical analysis. Each jar with 2 adults was considered an experimental replicate in data analysis. Dependent variables were numbers of female, male, deformed and ephippial offspring per adult female per day (number•female$^-$$^1$•day$^{-1}$) and the Jackknife pseudovalues of r. Effects of treatment level were analyzed by ANCOVA with longevity as a covariate. ANCOVA allowed the separation of the portions of the observed effects into two parts: that which was due to treatment, and that which was due to differences in longevity. Since Daphnia tend to produce ephippia in later clutches, decreases in average daily production of ephippia can be attributed to early mortality or lower output. The production of females, males, ephippia and deformed offspring for replicates that produced at least one clutch, and r for all replicates were analyzed. All analyses were done with the SYSTAT version 5.0 statistical package (SYSTAT for Windows: DATA, Version 5 Edition, 187 pp., Evanston, Ill., SYSTAT, Inc. (1992)).

Results

Figure 2A:
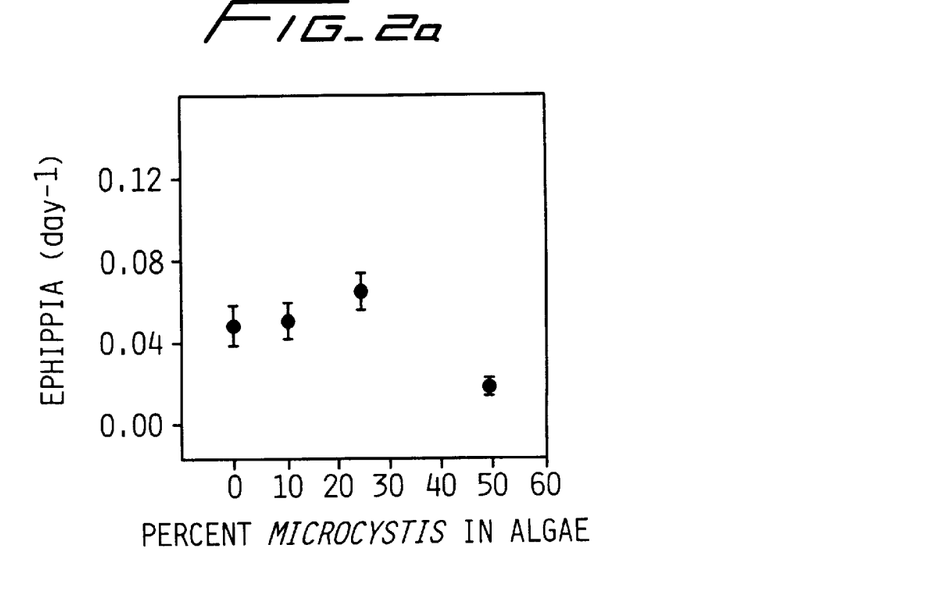
FIGS. 2(a)–(d) are graphical illustrations of the results of the Microcystis experiment. All data are numbers of offspring per female per day. Bars (I) are standard errors.
Figure 2B:
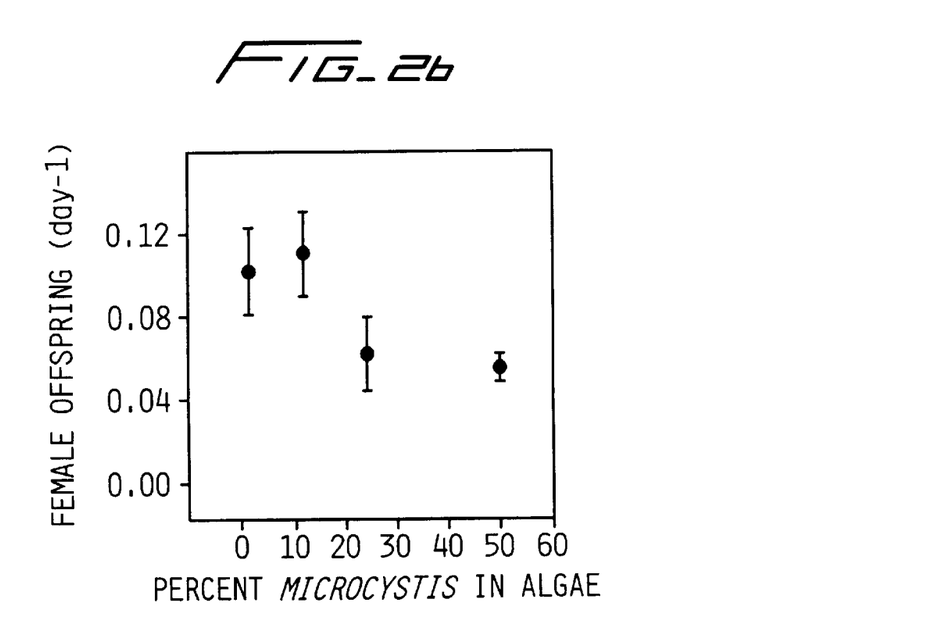

Microcystis experiment. The results of the Microcystis experiment are shown in FIG. 2. No significant differences in production of offspring for animals grown with less than 25% Microcystis in their diets was found. Between 25% and 50% Microcystis, daily ephippia production decreased by two thirds (FIG. 2a).

Figure 2C:
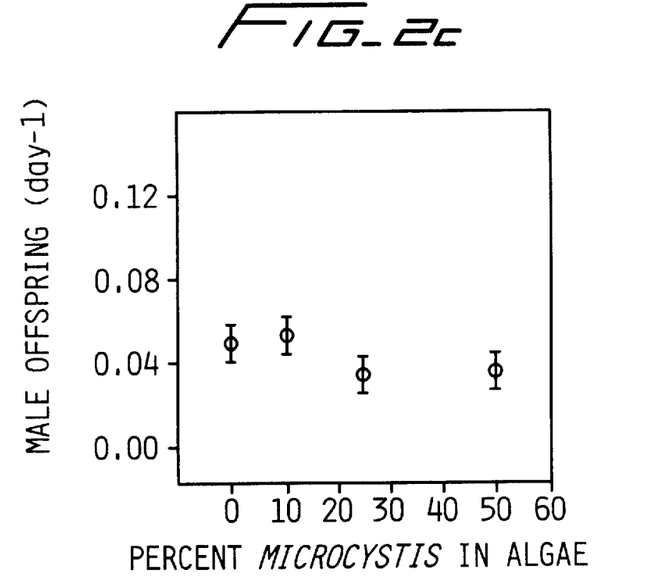

Results of the ANCOVA shown below in TABLE 4 indicate that longevity did not play a large role in the effect on ephippia production, and the decrease was therefore attributed to an actual reduction in average daily output. Numbers of female offspring decreased in a step fashion from 25% to 50% Microcystis (FIG. 2b) and male offspring were not affected at any level (FIG. 2c). Longevity explained a large part of the reduction in production of female offspring (TABLE 4). The effect of increasing concentrations of Microcystis on ephippia production was considerably more dramatic than on either male or female production.

TABLE 4[1]

| Dependent Variable | Source | df | ss | ms | F | P |
|---|---|---|---|---|---|---|
| Females | Treatment | 3 | .015 | .005 | 1.367 | .265 |
| n = 51 | Longevity | 1 | .030 | .030 | 8.182 | .006 |
| Males | Treatment | 3 | .003 | .001 | 1.245 | *.304* |
| n = 51 | Longevity | 1 | .000 | .000 | .042 | *.838* |
| Ephippia | Treatment | 3 | .008 | .003 | 3.019 | *.039* |
| n = 51 | Longevity | 1 | .002 | .002 | 2.483 | *.122* |
| r | Treatment | 3 | .001 | .000 | .315 | .815 |
| n = 60 | Longevity | 1 | .008 | .008 | 5.01 | .030 |

[1]P values of variables for which the data violate the assumption of normality are italicized.

The assumption of normality was tested by a Lillefiore's test and significant departures in production of females and ephippia were found. The assumption of homogeneity of variance was tested by dividing the largest sample variance by the smallest; it did not exceed 9 in any case. ANCOVA is robust to such violations of assumptions (J. F. Zolman, *Biostatistics*, Oxford University Press, Oxford, U.K. (1993)).

Figure 3A:
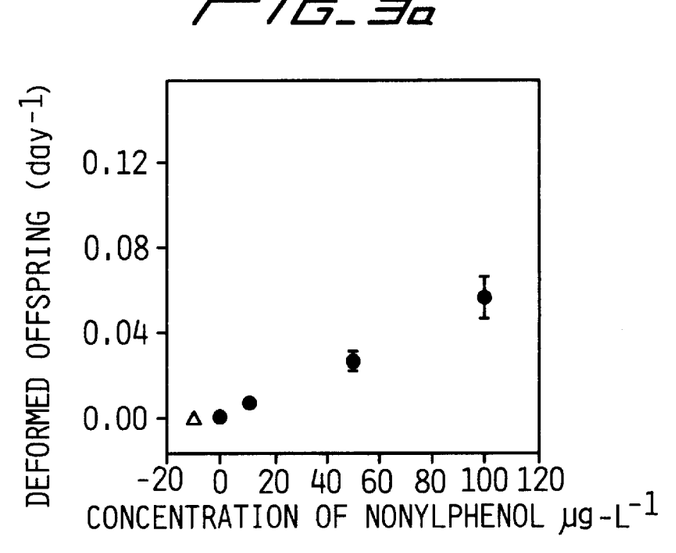
FIGS. 3(a)–(e) are graphical illustrations of the results of the nonylphenol experiment. Notation is the same as in FIG. 2. The open triangle ($\Delta$) is the acetone control.

Nonylphenol experiment. Microcystis and nonylphenol produced qualitatively different results, as shown in FIG. 3. A clear dose response to nonylphenol was seen in the production of deformed live offspring (P<0.001; FIG. 3a).

Figure 3B:
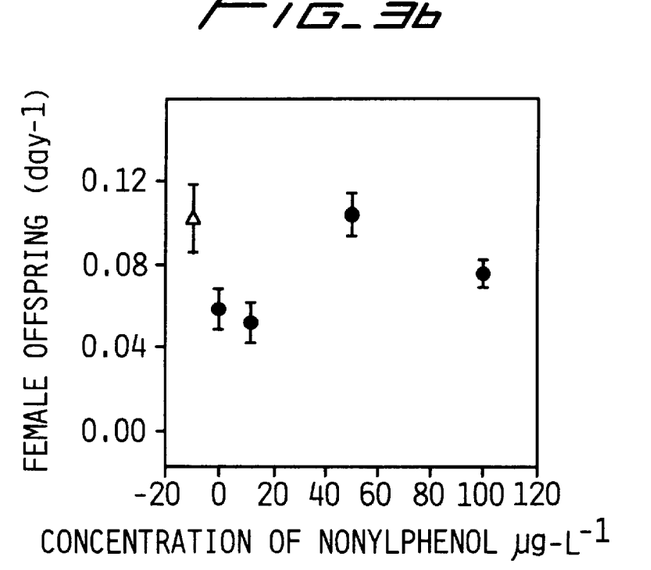
Figure 3C:
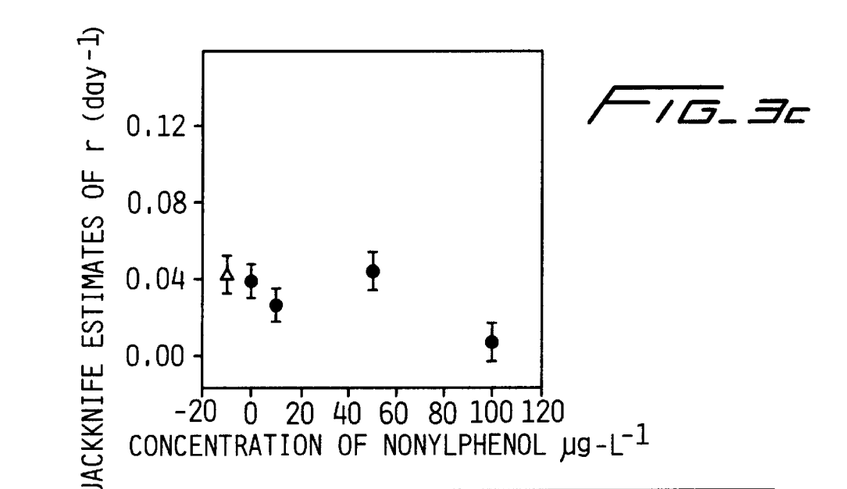
Figure 3D:
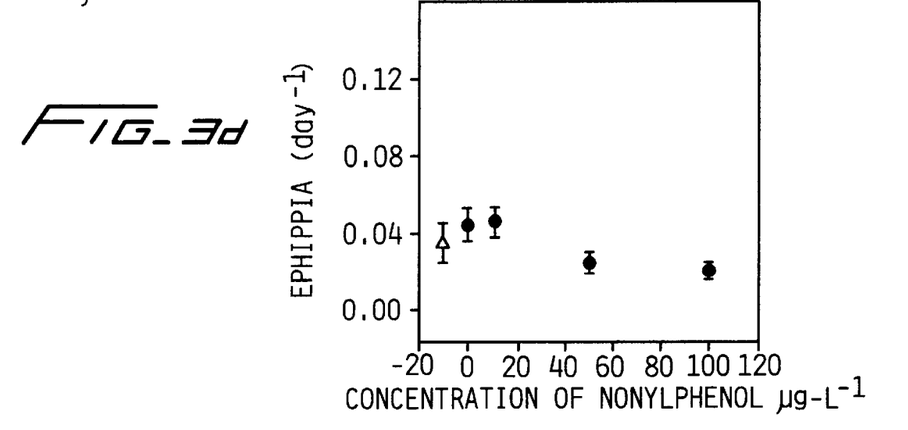
Figure 3E:
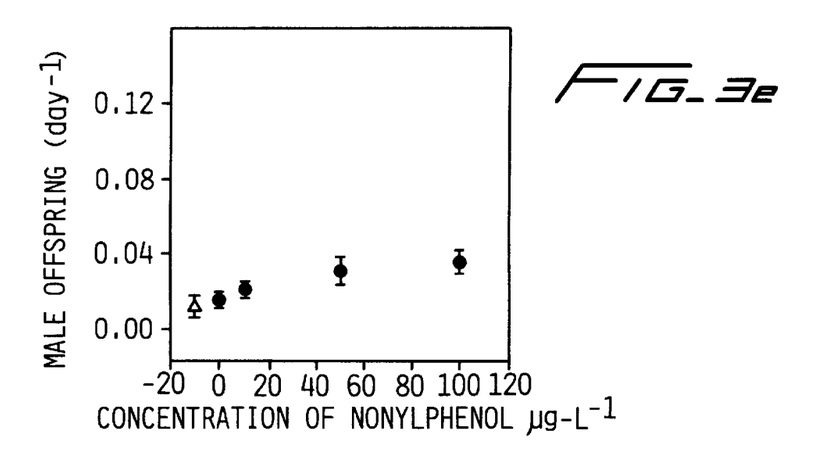

Results of the ANCOVA shown below in TABLE 5 indicate that the effect on deformed offspring was not a product of reduced longevity. Daily production of females increased at high dosages and in the presence of the acetone solvent (FIG. 3b). Reductions in r and in ephippia production were largely a result of increased adult mortality (FIG. 3c and d; TABLE 5). Numbers of male offspring were not affected at any level (FIG. 3e). The inverse dose response to nonylphenol in female production was unexpected, however the strongly linear pattern in deformed offspring with respect to dose lends confidence that exposure levels were reliable.

TABLE 5[1]

| Dependent Variable | Source | df | ss | ms | F | P |
|---|---|---|---|---|---|---|
| Females | Treatment | 4 | .024 | .006 | 3.700 | *.011* |
| n = 49 | Longevity | 1 | .002 | .002 | 1.273 | .265 |
| Males | Treatment | 4 | .002 | .000 | .899 | *.473* |
| n = 49 | Longevity | 1 | .000 | .000 | .108 | *.744* |
| Ephippia | Treatment | 4 | .007 | .002 | 2.340 | *.070* |
| n = 49 | Longevity | 1 | .005 | .005 | 6.986 | *.011* |
| Deformed | Treatment | 4 | .018 | .005 | 18.115 | .000 |
| n = 49 | Longevity | 1 | .001 | .001 | 3.190 | *.081* |
| r | Treatment | 4 | .007 | .002 | 3.168 | *.019* |
| n = 78 | Longevity | 1 | .067 | .067 | 119.18 | .000 |

[1]P values of variables for which the data violate the assumption of normality are italicized.

Figure 2D:
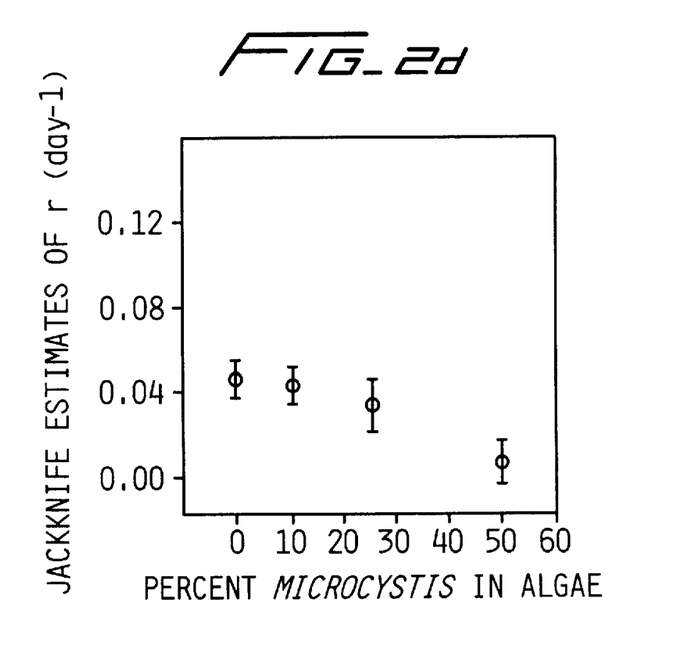

Life table results. Population growth rates differed among treatments in both experiments. r decreased steadily with increasing concentration of Microcystis (FIG. 2d). In the nonylphenol experiment, r was predictably sensitive to production of female offspring and showed a nonlinear pattern (FIG. 3c). No correlation was found between the Jackknife pseudovalues of r and production of deformed neonates (Kendall's rank coefficient of correlation, τ=−0.057, P>0.1). Therefore, the decrease in r was not a product of the omission of deformed offspring.

Figure 4A:
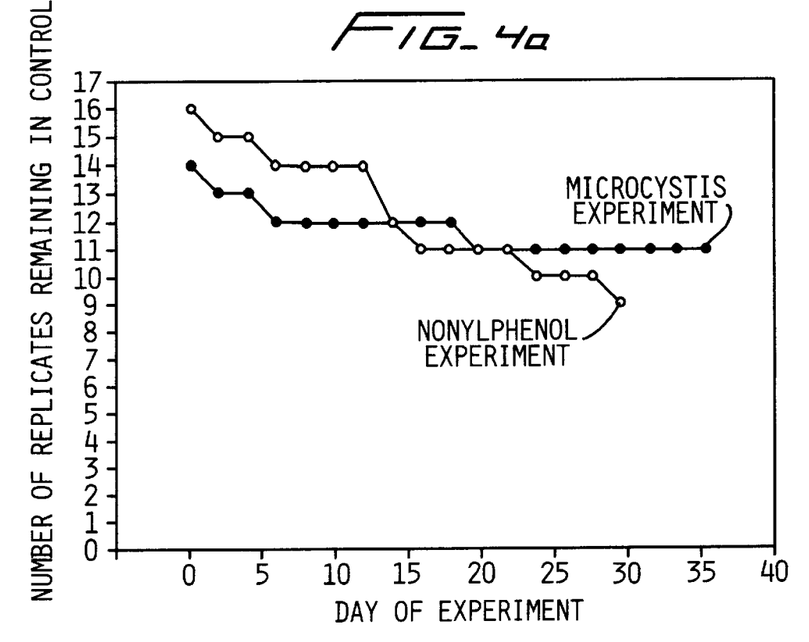
FIGS. 4(a)–(b) are graphical comparisons of the medium controls in the Microcystis and nonylphenol experiments.
Figure 4B:
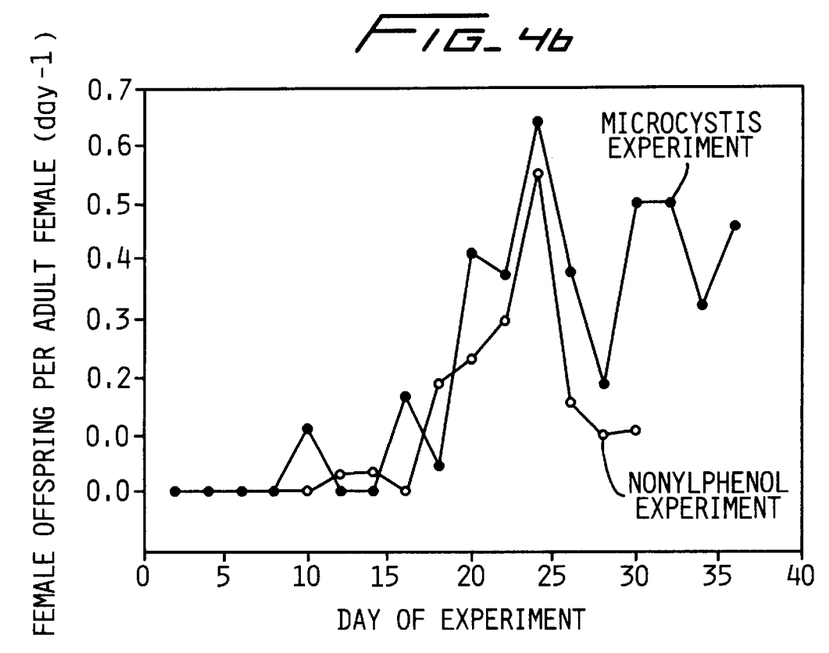

Decreases in male and female production and in r in the medium control of the nonylphenol experiment compared to the Microcystis experiment was observed despite nearly identical growing conditions (the food level was slightly higher in the nonylphenol experiment, see Methods). FIG. 4 illustrates that both survivorship and fecundity were lower in the nonylphenol experiment than the Microcystis experiment. Therefore, both contributed to lower r in the nonylphenol experiment control.

Discussion

As shown in this assay, chemical stress can have complex effects on Daphnia populations that undergo periodic sexual reproduction. Production of males, females and ephippia were sensitive to different levels of contamination and were affected both by changes in average daily output and by shorter life spans of the animals. The two stressors, Microcystis and nonylphenol, affected *Daphnia galeatamendotae's* production of females, males and ephippia in different ways. Changes in the abundances of each of the three reproductive forms of Daphnia will have unique effects on a population's growth and persistence.

Microcystis. In the presence of cyanobacteria, there is an increase in production of ephippia and a decrease in fecundity in female offspring. The results show that Daphnia's ability to produce ephippia will be limited if the sexual phase of Daphnia's life cycle takes place under severe stress from cyanobacteria. Reduced production by females and depressed population growth rate, r, both result in a lower supply of ephippia to the resting egg bank. The levels of Microcystis used were environmentally realistic for a eutrophic lake. The biovolume of Microcystis in the highest treatment level (4.55 $\mu$L-L$^{-1}$) was in the range (2–17 $\mu$L-L$^{-1}$) observed on 4% of sampling dates in Lake Mendota, Wis. from 1976–89. However, cyanobacteria as a group were present at >2 $\mu$L-L$^{-1}$ on 16% of sampling dates from the same period, and reached a maximum concentration of 17 $\mu$L-L$^{-1}$. This indicates that Daphnia are likely to encounter cyanobacteria at levels that inhibit ephippia production.

A dramatic decrease in ephippia output at 50% Microcystis was observed (FIG. 2c). Growing conditions were chosen for maximal induction of males and ephippia, and the clone that was used may have been unable to allocate further effort to ephippia. Although under some conditions Daphnia increase ephippia production when exposed to stress from cyanobacteria, when conditions favor production of males and ephippia (short day length, low food, high densities of animals), ephippia are more heavily reduced than live young by toxic chemical defenses.

Nonylphenol. High doses of nonylphenol increased female offspring production while numbers of ephippia decreased slightly and male production remained constant. The solvent control (80 $\mu$g-L$^{-1}$ acetone) showed greater production of female offspring than the medium control (FIG. 3b). This was due to sensitivity of the clone to acetone, and/or a heightened sensitivity to nonylphenol or its interaction with acetone due to exposure to sex-inducing environmental stresses.

There was a lack of pattern for female production with respect to dose of nonylphenol. First, the difference between the medium and solvent controls indicates that the effect of acetone was not negligible and that an interaction between dose of nonylphenol and acetone may have been important. Second, inverse dose responses characterize the activity of some chemicals, such as endocrine disrupters, which can interact with multiple physiological processes. The mechanism of activity of chemicals such as nonylphenol that affect endocrine function changes with exposure levels, causing one biological effect to be replaced by another as dose increases. The pattern for female offspring production and the deformity associated with nonylphenol indicates that direct chemical interactions with developmental processes occur in Daphnia, as well as in a wide range of vertebrates.

Development. Prenatal exposure to nonylphenol caused a nonlethal but disabling abnormality at the stage where Daphnia develop from embryos into juveniles. The deformity was seen in 11% of live young grown at 10 $\mu$gL-L$^{-1}$ nonylphenol, below the "no-observed effect concentration" (NOEC) of nonylphenol for *D. magna* of 24 $\mu$gL-L$^{-1}$ and within the range commonly found in waters that receive sewage effluent. Only animals that were prenatally exposed to nonylphenol exhibited the deformity, indicating that Daphnia are especially vulnerable to chemical interference at early developmental stages. Nonylphenol consistently affected morphological development of tail spines and swimming setae, suggesting that its activity involves specific ontogenetic processes.

Life tables. Short term population dynamics of asexual females were affected by exposure to both Microcystis and nonylphenol. Depression of r lowers the population of adults that can contribute ephippia and can affect trophic interactions with Daphnia's resources and consumers. The two experiments illustrate that effects on r occur independently of effects on male and ephippial young.

What is claimed is:

1. A bioassay for detecting a substance that interferes with endocrine function in an animal, comprising:

a) providing a test sample and a control medium, each containing an effective amount of minerals, trace elements and a food source to maintain adult and neonate Daphnia growth and survival for an at least 3-day period; and the test sample containing a sample to be tested;

b) placing at least three adult, oviparous Daphnia of a single clone into each of the test sample and the control medium;

c) maintaining the test sample and the control medium for a time period effective to optimize exposure of offspring to the test sample and the control medium, under growth conditions of temperature and photoperiod to induce sexual reproduction in Daphnia;

d) measuring the following endpoints in the test sample and the control to provide a set of data:
      (i) survivorship of adults and neonates; and
      (ii) number of females;
   and one or more of the following endpoints:
      (iii) number of males;
      (iv) number of resting eggs; and
      (v) number of offspring displaying a morphological abnormality;

e) analyzing the data for a variance in the endpoints between the test sample and the control; and f) determining the presence or absence of an endocrine-interfering substance based on the variance in the endpoints between the test sample and the control in step e).

2. The bioassay according to claim 1, wherein the Daphnia clone produces about 30–70% males of the total offspring under the control conditions.

3. The bioassay according to claim 1, wherein the Daphnia clone is derived from *Daphnia galeata-mendotae* or *Daphnia pulex*.

4. The bioassay according to claim 3, wherein the Daphnia clone is derived from *Daphnia galeata-mendotae*.

5. The bioassay according to claim 4, wherein the Daphnia clone is derived from *Daphnia galeata-mendotae* Wingra clone CDF-1.

6. The bioassay according to claim 1, wherein step c) comprises maintaining the test sample and control at a temperature of about 18–21° C. and under a light:dark photoperiod of about 9:15 hours.

7. The bioassay according to claim 1, wherein the morphological deformity in step d) is identified by reduced or absent terminal setae on the second antennae, a forward curved tail spine, reduced swimming ability, or a combination thereof.

8. The bioassay according to claim 1, wherein the presence of an endocrine disrupter substance is indicated by a variance between the test sample and the control of the male:female sex ratio, the ratio of males:total offspring, the number of resting eggs, the number of neonates with a morphological abnormality, or a combination thereof.

9. The bioassay according to claim 1, wherein the aqueous sample is from a natural water source, industrial effluent, municipal effluent, sewage effluent, or a synthetic testing medium.

10. The bioassay according to claim 1, wherein the substance is an herbicide, insecticide, fungicide, xenobiotic, plasticizer, phytohormone, phytoestrogen, organic solvent, or a combination thereof.

11. The bioassay according to claim 8, wherein the substance has estrogen-mimicking properties.

12. The bioassay according to claim 11, wherein the estrogen-mimicking compound is selected from the group consisting of estradiol, diethylstilbestrol, kepone, dichlorodiphenyltrichloroethane, dichlorodiphenyldichloroethane, 1-hydroxychlordene, chlordane, zearalenone, coumestrol, nonylphenol, butylphenol, pentylphenol, isopentylphenol, polychlorinated biphenyl, chlorpyrifos, pentachlorophenol, atrazine, carbaryl, endosulfan, ethanol, and derivatives thereof.

13. The bioassay according to claim 1, wherein the test sample is prepared as a series of dilutions of the sample to be tested.

14. The bioassay according to claim 1, wherein step c) further comprises changing the growth medium in the test sample and the control on day 3–4 of the test period.

15. The bioassay according to claim 1, further comprising: step g) conducting an additional assay to determine the identity of the endocrine disrupting substance in the test sample.

16. The bioassay according to claim 1, wherein the Daphnia clone produces about 15–70% males of the total offspring under the control conditions.

17. A bioassay for detecting a biologically-active level of a substance that interferes with endocrine function in an animal, comprising:

a) combining a control and a test sample with a plurality of adult, oviparous Daphnia derived from a single clone, under suboptimal growth conditions of temperature and photoperiod and for a time effective to induce sexual reproduction;

b) measuring in the test sample and the control, the following endpoints to provide a set of data:
      (i) survivorship of adults and neonates;
      (ii) number of females;

and one or more of the following endpoints:
      (iii) number of males;
      (iv) number of resting eggs; and
      (v) number of offspring displaying a morphological abnormality;

c) analyzing the data for a variance in the endpoints between the test sample and the control; and d) determining the presence or absence of an endocrine-interfering substance based on the variance in the endpoints between the test sample and the control.

18. A kit for use in conducting a Daphnia reproductive bioassay on an aqueous sample to detect a substance that interferes with endocrine function in an animal, comprising, in association:

a culture of a clone of Daphnia capable of producing at least about 30–70% males of the total offspring under control conditions;

instructions for conducting the Daphnia bioassay according to claim 17;

an algal food source for the Daphnia; and a growth medium for culturing the Daphnia.

19. The kit according to claim 18, further comprising:

a container for the test sample and the control; a container for observing the Daphnia; a device for manipulating the Daphnia; or any combination thereof.

* * * * *